(12) United States Patent
Valero et al.

(10) Patent No.: US 11,241,370 B2
(45) Date of Patent: *Feb. 8, 2022

(54) METHOD OF PREPARING SILICAS, SILICAS WITH SPECIFIC PORE-SIZE AND/OR PARTICLE-SIZE DISTRIBUTIONS, AND THE USES THEREOF, IN PARTICULAR FOR REINFORCING POLYMERS

(75) Inventors: Rémi Valero, Lyons (FR); Julien Hernandez, Antony (FR)

(73) Assignee: RHODIA CHIMIE, Aubervilliers (FR)

( * ) Notice: Subject to any disclaimer, the term of this patent is extended or adjusted under 35 U.S.C. 154(b) by 456 days.

This patent is subject to a terminal disclaimer.

(21) Appl. No.: 13/166,458

(22) Filed: Jun. 22, 2011

(65) Prior Publication Data

US 2011/0263784 A1    Oct. 27, 2011

Related U.S. Application Data

(63) Continuation of application No. 12/461,689, filed on Aug. 20, 2009, now abandoned, which is a
(Continued)

(51) Int. Cl.
*C01B 33/12*    (2006.01)
*A61K 8/25*    (2006.01)
(Continued)

(52) U.S. Cl.
CPC ............ *A61K 8/25* (2013.01); *A61Q 11/00* (2013.01); *C01B 33/193* (2013.01); *C08K 3/36* (2013.01);
(Continued)

(58) Field of Classification Search
CPC .............. C01P 2004/61; C01P 2004/51; C01P 2004/32; C01P 2006/14; C01P 2006/16;
(Continued)

(56) References Cited

U.S. PATENT DOCUMENTS

| 5,547,502 A | 8/1996 | Chevallier et al. |
| 5,800,608 A * | 9/1998 | Bomal ................. C01B 33/193 106/492 |
| 6,180,076 B1 * | 1/2001 | Uhrlandt ............... C01B 33/193 423/335 |

FOREIGN PATENT DOCUMENTS

| EP | 0 520 862 | 12/1992 |
| EP | 0 745 558 | 12/1996 |

(Continued)

*Primary Examiner* — Smita S Patel
(74) *Attorney, Agent, or Firm* — Osha Bergman Watanabe & Burton LLP (57) ABSTRACT

The invention relates to a novel method of preparing silicas and to highly-structured silicas having the following characteristics: a specific surface area CTAB ($S_{CTAB}$) of between 40 and 525 m²/g; a specific surface area BET ($S_{BET}$) of between 45 and 550 m²/g; an object size distribution width Ld ((d84−D16)/d50), which is measured by XDC particle size analysis after deagglomeration with ultrasound, of at least 0.91; and a pore-size distribution such that ratio V(d5−d50)/V(d5−d100) is at least 0.66. The invention also relates to the use of said silicas as polymer reinforcing fillers.

35 Claims, 1 Drawing Sheet

Related U.S. Application Data continuation of application No. 10/486,573, filed as application No. PCT/FR02/02872 on Aug. 13, 2002, now abandoned.

(51) Int. Cl.
- *C01B 33/193* (2006.01)
- *C08K 3/36* (2006.01)
- *A61Q 11/00* (2006.01)
- *H01M 50/431* (2021.01)

(52) U.S. Cl.
CPC ..... *H01M 50/431* (2021.01); *A61K 2800/412* (2013.01); *C01P 2004/32* (2013.01); *C01P 2004/51* (2013.01); *C01P 2004/61* (2013.01); *C01P 2006/12* (2013.01); *C01P 2006/14* (2013.01); *C01P 2006/16* (2013.01); *C01P 2006/17* (2013.01); *C01P 2006/80* (2013.01); *C01P 2006/90* (2013.01); *Y10T 428/2982* (2015.01)

(58) Field of Classification Search
CPC .............. C01P 2006/12; C01P 2006/80; C01P 2006/90; C01P 2004/50; C01P 2006/17; C08K 3/36; A61K 2800/412; A61K 8/25; C01B 33/12; C01B 33/193; Y10T 428/2982; H01M 50/431; A61Q 11/00; C08L 27/06; C08L 2205/02; C08L 9/02; C08L 9/06; C08L 21/00; C02F 1/56

See application file for complete search history.

(56) References Cited

FOREIGN PATENT DOCUMENTS

| | | |
|---|---|---|
| WO | WO 97/46485 | 12/1997 |
| WO | WO 98/54090 | 12/1998 |
| WO | WO 01/07364 | 2/2001 |

* cited by examiner

METHOD OF PREPARING SILICAS, SILICAS WITH SPECIFIC PORE-SIZE AND/OR PARTICLE-SIZE DISTRIBUTIONS, AND THE USES THEREOF, IN PARTICULAR FOR REINFORCING POLYMERS

CROSS-REFERENCE TO RELATED APPLICATIONS

The present application is a Continuation of, and claims priority under 35 U.S.C. § 120 to, U.S. patent application Ser. No. 12/461,689, filed Aug. 20, 2009, which is a Divisional of, and claims priority under 35 U.S.C. § 120 to, U.S. application Ser. No. 10/486,573, filed on Feb. 11, 2004, which was a National Stage filing under 35 U.S.C. § 371 of International Application No. PCT/FR02/02872, filed Aug. 13, 2002, which claims priority under 35 U.S.C. § 119 to French Application No. 01/11001, filed Aug. 13, 2001. The entire contents of each of these applications are hereby incorporated by reference in this application.

BACKGROUND

The present invention relates to a novel process for preparing silica, to silicas having a particular particle size distribution and/or a particular pore distribution, especially in the form of powder, of approximately spherical beads or of granules, and to their applications, such as the reinforcement of polymers.

It is known to employ white reinforcing fillers in polymers, particularly in elastomers, such as for example precipitated silica.

SUMMARY

It is an object of the invention to provide, in particular, an alternative filler for polymer compositions, having a typical characteristics, also providing them with a highly satisfactory compromise of properties, in particular as regards their mechanical and dynamic properties, without impairing their Theological properties.

The invention firstly provides a novel process for preparing silica, of the type comprising the reaction of a silicate with an acidifying agent whereby a silica suspension is obtained, followed by the separation and the drying of this suspension, characterized in that the reaction of the silicate with the acidifying agent is carried out according to the following successive steps:

(i) an aqueous stock having a pH of between 2 and 5 is formed;

(ii) silicate and acidifying agent are added simultaneously to the said stock in such a way that the pH of the reaction mixture is maintained between 2 and 5;

(iii) the addition of the acidifying agent is stopped, while continuing to add silicate into the reaction mixture until a pH value of the reaction mixture of between 7 and 10 is obtained;

(iv) silicate and acidifying agent are added simultaneously to the reaction mixture in such a way that the pH of the reaction mixture is maintained between 7 and 10; and (v) the addition of the silicate is stopped, while continuing to add the acidifying agent into the reaction mixture until a pH value of the reaction mixture of less than 6 is obtained.

Thus, it has been found that the succession of particular steps, in particular the presence of a first simultaneous addition of acidifying agent and silicate in an acid medium at pH between 2 and 5 and of a second simultaneous addition of acidifying agent and silicate in a basic medium of pH between 7 and 10, constitute important conditions for giving the products obtained their particular characteristics and properties.

The acidifying agent and the silicate are chosen in a manner well known per se.

As acidifying agent, a strong mineral acid, such as sulphuric acid, nitric acid or hydrochloric acid, or an organic acid, such as acetic acid, formic acid or carbonic acid, will in general be used.

The acidifying agent may be dilute or concentrated; its normality may be between 0.4 and 36N, for example between 0.6 and 1.5N.

In particular, in the case in which the acidifying agent is sulphuric acid, its concentration may be between 40 and 180 g/l, for example between 60 and 130 g/l.

However, as silicate, it is possible to use any standard form of silicates such as metasilicates, disilicates and, advantageously, an alkali metal silicate, especially sodium or potassium silicate.

The silicate may have a concentration (expressed as $SiO_2$ content) of between 40 and 3-30 g/l, for example between 60 and 300 g/l, in particular between 60 and 260 g/l.

In general, sulphuric acid will generally be employed as the acidifying agent, and sodium silicate as silicate.

If sodium silicate is used, this is generally present with an $SiO_2/Na_2O$ weight ratio of between 2.5 and 4, for example between 3.2 and 3.8.

DETAILED DESCRIPTION

With regard more particularly to the preparation process of the invention, the reaction between the silicate and the acidifying agent takes place in a very specific manner according to the following steps.

Firstly, an aqueous stock having a pH of between 2 and 5 is formed.

Preferably, the stock formed has a pH of between 2.5 and 5, especially between 3 and 4.5; this pH is, for example, between 3.5 and 4.5.

This initial stock may be obtained by addition of acidifying agent to water so as to obtain a pH value of the stock between 2 and 5, preferably between 2.5 and 5, especially between 3 and 4.5, and for example between 3.5 and 4.5.

It may also be obtained by addition of acidifying agent to a water+silicate mixture so as to obtain this pH value.

It may also be prepared by addition of acidifying agent to a stock containing preformed silica particles at a pH of less than 7, so as to obtain a pH value between 2 and 5, preferably between 2.5 and 5, especially between 3 and 4.5 and for example between 3.5 and 4.5.

The stock formed in step (i) may optionally include an electrolyte. However, it is preferable for no electrolyte to be added during the preparation process, in particular in step (i).

The term "electrolyte" is understood here in its normally accepted meaning, that is to say it means any ionic or molecular substance which, when it is in solution, decomposes or dissociates to form ions or charged particles. As electrolyte, mention may be made of a salt of the group of alkali-metal and alkaline-earth metal salts, especially the salt of the metal of the initial silicate and of the acidifying agent, for example sodium chloride in the case of the reaction of a sodium silicate with hydrochloric acid or, preferably, sodium sulphate in the case of the reaction of a sodium silicate with sulphuric acid.

The second step (step (ii)) consists of a simultaneous addition of acidifying agent and of silicate in such a way (in particular with such flow rates) that the pH of the reaction mixture is maintained between 2 and 5, preferably between 2.5 and 5, especially between 3 and 4.5, for example between 3.5 and 4.5.

This simultaneous addition is advantageously carried out in such a way that the pH value of the reaction mixture is always equal (to within ±0.2) to that reached at the end of the initial step (i).

Next, in a step (iii), the addition of the acidifying agent is stopped, while continuing to add silicate into the reaction mixture so as to obtain a pH value of the reaction mixture of between 7 and 10, preferably between 7.5 and 9.5.

It may then be advantageous for the reaction mixture, just after this step (iii) and therefore just after the addition of silicate has been stopped, to undergo a maturing step, especially at the pH obtained after step (iii), and in general with stirring; this maturing step may, for example, last 2 to 45 minutes, in particular from 5 to 25 minutes, and preferably includes neither addition of acidifying agent nor addition of silicate.

After step (iii) and the optional maturing step, acidifying agent and silicate are again simultaneously added in such a manner (in particular with such flow rates) that the pH of the reaction mixture is maintained between 7 and 10, preferably between 7.5 and 9.5.

This second simultaneous addition (step (iv)) is advantageously carried out in such a way that the pH value of the reaction mixture is always equal (to within ±0.2) to that achieved after the preceding step.

It should be noted that it is possible, between step (ii) and step (iv), for example between, on the one hand, the optional maturing step following step (iii) and, on the other hand, step (iv), to add acidifying agent to the reaction mixture, the pH of the reaction mixture after this addition of acidifying agent being, however, between 7 and 9.5, preferably between 7.5 and 9.5.

Finally, in a step (v), the addition of the silicate is stopped, while continuing to add acidifying agent into the reaction mixture so as to obtain a pH value of the reaction mixture of less than 6, preferably between 3 and 5.5, in particular between 3 and 5, for example between 3 and 4.5.

It may then be advantageous, after this step (v) and therefore just after stopping the addition of acidifying agent, for the reaction mixture to undergo a maturing step, especially at the pH obtained after step (v), and in general with stirring; this maturing step may last, for example, from 2 to 45 minutes, in particular from 5 to 20 minutes, and preferably includes no addition of acidifying agent nor addition of silicate.

The reaction vessel in which the entire reaction between the silicate and the acidifying agent takes place is usually fitted with suitable stirring equipment and with suitable heating equipment.

The entire reaction between the silicate and the acidifying agent is generally carried out between 70 and 95° C., in particular between 75 and 90° C.

According to a variant of the invention, the entire reaction between the silicate and the acidifying agent is carried out at a constant temperature, usually between 70 and 95° C., in particular between 75 and 90° C.

According to another variant of the invention, the temperature at the end of the reaction is higher than the temperature at the start of the reaction: thus, the temperature at the start of the reaction is preferably maintained (for example during steps (i) to (iii)) at between 70 and 85° C., and then the temperature is increased, preferably up to a value between 85 and 95° C., at which value it is maintained (for example during steps (iv) and (v)) until the end of the reaction.

After the steps that have just been described, a silica slurry is obtained, which is then separated (by liquid-solid separation).

The separation used in the preparation-process according to the invention usually comprises filtration followed, if necessary, by washing. The filtration is carried out using any suitable method, for example by means of a filter press, a band filter or a vacuum filter.

The silica suspension thus recovered (the filter cake) is then dried.

This drying may be carried out using any means known per se.

Preferably, the drying is spray drying. For this purpose, any suitable type of spray dryer may be used, especially a turbine, nozzle, liquid-pressure or two-fluid type spray dryer. In general, when the filtration is carried out by means of a filter press, a nozzle spray dryer is used, and when the filtration is carried out by means of a vacuum filter, a turbine spray dryer is used.

It should be noted that the filter cake is not always under conditions allowing spray drying, especially because of its high viscosity. In a manner known per se, the cake is then subjected to a disintegration operation. This operation may be carried out mechanically, by passing the cake through a colloidal-type mill or a ball mill. The disintegration is generally carried out in the presence of an aluminium compound, in particular sodium aluminate, and optionally in the presence of an acidifying agent, as described above (in the latter case, the aluminium compound and the acidifying agent are generally added simultaneously). The disintegration operation makes it possible in particular to lower the viscosity of the suspension to be subsequently dried.

When the drying is carried out by means of a nozzle spray dryer, the silica that can then be obtained is usually in the form of approximately spherical beads.

After the drying, a milling step may then be carried out on the recovered product. The silica that can then be obtained is generally in the form of a powder.

When the drying is carried out by means of a turbine spray dryer, the silica that can then be obtained may be in the form of a powder.

Finally, the product, dried (especially by a turbine spray dryer) or milled as indicated above, may optionally be subjected to an agglomeration step which consists, for example, of direct compression, wet granulation (that is to say with the use of a binder such as water, a silica suspension, etc.), extrusion or, preferably, dry compacting. When the latter technique is used, it may prove opportune, before carrying out the compacting operation, for the pulverulent products to undergo de-aeration (an operation also called predensification or degassing) so as to remove the air included in the products and to ensure that they are more uniformly compacted.

The silica that can then be obtained by this agglomeration step is generally in the form of granules.

The silica powders, like the silica beads, obtained by the process according to the invention thus offer the advantage inter alia of obtaining granules in a simple, effective and economic manner, especially by conventional forming operations, such as for example granulation or compacting, without these operations causing any degradation liable to mask, or even destroy, the good intrinsic properties that these powders or these beads have, as may be the case in the prior art when processing conventional powders.

The preparation process according to the invention makes it possible in particular to obtain silicas more of the precipitative-silica type which, on the one hand, are highly structured and non-friable and, on the other hand, generally have a high dispersibility in polymers, give the latter a very satisfactory compromise of properties, in particular as regards their dynamic and mechanical properties (especially a good reinforcing effect and very good abrasion resistance), without impairing their Theological properties. The silicas obtained preferably have a particular particle size distribution and/or pore distribution.

The silicas that can be obtained by the process of the invention constitute one of the aspects of the present invention.

Further objects of the invention consist of novel silicas, more of the precipitated-silica type, which are highly structured and possess a specific particle size distribution and/or a particular pore distribution; furthermore, they generally have good dispersibility in polymers, give the latter a very satisfactory compromise of properties, in particular as regards their dynamic properties (especially a reduction in the strain energy dissipation (low Payne effect), low hysteresis losses at high temperature (especially a reduction in tan δ at 60° C.) without impairing their rheological properties (and therefore without impairing their processability/formability (for example, a lower green viscosity for the same specific surface area)) and possess good mechanical properties, in particular a good reinforcing effect, especially in terms of moduli, and very good abrasion resistance, hence improved wear resistance in the case of finished articles based on the said polymers.

In the description that follows, the BET specific surface area is determined using the Brunauer-Emmet-Teller method described in "The Journal of the American Chemical Society", Vol. 60, page 309, February 1938 and corresponding to the International Standard ISO 5794/1 (Appendix D).

The CTAB specific surface area is the external surface area determined according to the NF T 45007 (November 1987) (5.12) standard.

The DOP oil uptake is determined according to the NF T 30-022 (March 1953) standard using dioctyl phthalate.

The pH is measured according to the ISO 787/9 standard (the pH of a 5% suspension in water).

The XDC particle size analysis method, using centrifugal sedimentation, by which, on the one hand, the size distribution widths of silica objects and, on the other hand, the XDC mode illustrating its size of objects were measured, is described below.

Equipment Needed:
BI-XDC (Brookhaven Instrument X Disc Centrifuge) centrifugal sedimentation particle size analyser sold by Brookhaven Instrument Corporation;
50 ml tall form beaker;
50 ml graduated measuring cylinder; P1 1500 watt Branson ultrasonic probe, with no endpiece, 13 mm in diameter;
deionized water;
ice-filled crystallizer;
magnetic stirrer.
Measurement Conditions:
DOS 1.35 version of the software (supplied by the manufacturer of the particle size analyser);
fixed mode;
rotation speed;
duration of the analysis: 120 minutes;
density (silica): 2.1;
volume of the suspension to be sampled: 15 ml.
Preparation of the Specimen:
add 3.2 g of silica and 40 ml deionized water to the tall form beaker;
put the beaker containing the suspension in the ice-filled crystallizer;
immerse the ultrasonic probe in the beaker;
disintegrate the suspension for 16 minutes using the 1500 watt Branson probe (used at 60% of maximum power);
after the disintegration, put the beaker on a magnetic stirrer.
Preparation of the Particle Size Analyser:
turn the apparatus on and leave to heat for 30 minutes;
rinse the disc twice with deionized water;
introduce 15 ml of the specimen to be analysed into the disc and start the stirring;
enter into the software the above-mentioned measurement conditions;
make the measurements;
when the measurements have been taken:
stop the disc rotating;
rinse the disc several times with deionized water;
stop the apparatus.
Results In the apparatus register, record the values of the 16 wt %, 50 wt % (or median) and 84 wt let-through diameters and the value of the mode (the derivative of the cumulative particle size curve gives a frequency curve the abscissa of the maximum of which (abscissa of the main population) is called the mode).

The size distribution width $L_d$ of objects, measured by XDC particle size analysis, after ultrasonic disintegration (in water), corresponds to the (d84−d16)/d50 ratio in which dn is the size for which n % of particles (by weight) have a size smaller than that size (the distribution width $L_d$ is therefore calculated from the cumulative particle size curve taken in its entirety).

The size distribution width $L'_d$ of objects smaller than 500 nm, measured by XDC particle size analysis, after ultrasonic disintegration (in water), corresponds to the (d84−d16)/d50 ratio in which dn is the size for which n % of particles (by weight), with respect to the particles smaller in size than 500 nm, have a size smaller than that size (the distribution width $L'_d$ is therefore calculated from the cumulative particle size curve truncated above 500 nm).

In addition, using this centrifugal sedimentation XDC particle size analysis method, it is possible to measure a weight-average size of the particles (that is to say of the secondary particles or aggregates), denoted $d_w$, after dispersion, by ultrasonic disintegration, of the silica in water. The method differs from that described above by the fact that the suspension formed (silica+deionized water) is disintegrated, on the one hand, for 8 minutes and, on the other hand, using a 1500 watt 1.9 cm VIBRACELL ultrasonic probe (sold by Bioblock) (the probe being used at 60% of maximum power). After analysis (sedimentation for 120 minutes), the weight distribution of particle sizes is calculated by the software of the particle size analyser. The weight-average geometrical mean of the particle sizes (Xg according to the nomenclature of the software), denoted $d_w$, is calculated by the software from the following equation:

$$\log d_W = \sum_1^n m_i \log d_i \Big/ \sum_1^n m_i,$$

$m_i$ being the mass of all of the objects in the class of size $d_i$.

The pore volumes given are measured by mercury porosimetry; each specimen is prepared as follows: each specimen is predried for 2 hours in an oven at 200° C. and then placed in a test container within 5 minutes following its removal from the oven and vacuum-degassed, for example using a rotary vane pump; the pore diameters (AUTOPORE III 9420 Micromeritics porosimeter) are calculated by the Washburn equation with a contact angle θ of 140° and a surface tension γ of 484 dynes/cm (or N/m).

$V_{(d5-d50)}$ represents the pore volume formed by the pores of diameters between d5 and d50 and $V_{(d5-d100)}$ represents the pore volume formed by the pores of diameters between d5 and d100, do here being the pore diameter for which n % of the total surface area of all the pores is formed by the pores of diameter greater than that diameter (the total surface area of the pores ($S_0$) may be determined from the mercury intrusion curve).

Figure 1:
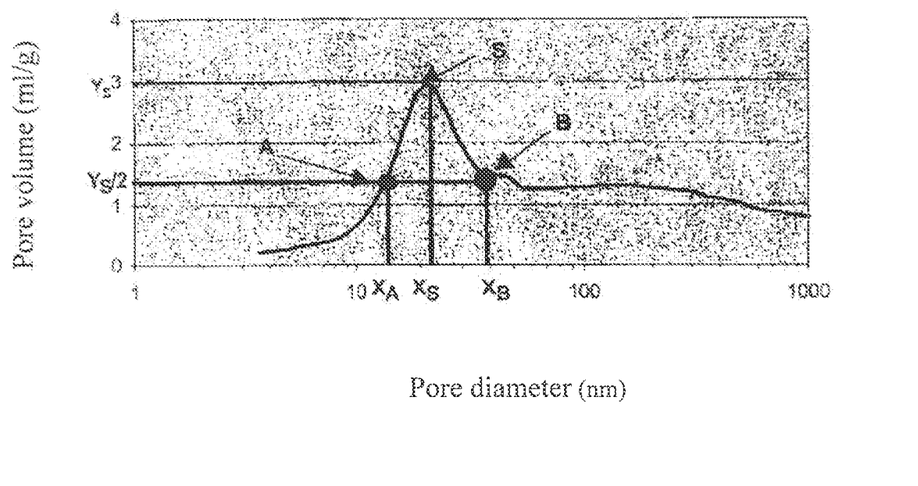
The FIGURE is a pore distribution curve for a material of the present invention.

The pore distribution width ldp is obtained by the pore distribution curve, as indicated in FIG. 1, i.e., the pore volume (in ml/g) as a function of the pore diameter (in nm): the coordinates of the point S corresponding to the principal population, namely the values of the diameter $X_S$ (in nm) and the pore volume $Y_S$ (in ml/g), are recorded; a straight line of the equation $Y=Y_S/2$ is plotted; this straight line cuts the pore distribution curve at two points A and B on either side of $X_S$, the abscissae (in nm) of points A and B being $X_A$ and $X_B$, respectively; the pore distribution width ldp is equal to the ratio $(X_A-X_B)/X_S$.

In some cases, the dispersibility (and disintegratability) of the silicas according to the invention may be quantified by means of specific disintegration tests.

One of the disintegration tests is carried out according to the following protocol:

The cohesion of the agglomerates is assessed by a particle size measurement (using laser diffraction) carried out on a suspension of silica ultrasonically disintegrated beforehand; in this way, the disintegratability of the silica (the break-up of objects from 0.1 to a few tens of microns) is measured.

The ultrasonic disintegration is carried out using a Bioblock Vibracell sonifier (600-W) fitted with a 19 mm diameter probe. The particle size measurement is carried out by laser diffraction on a SYMPATEC particle size analyser.

Weighed in a pillbox (height: 6 cm and diameter: 4 cm) are 2 grams of silica to which 50 grams of deionized water are added: an aqueous suspension containing 4% silica, which is homogenized for 2 minutes by magnetic stirring, is thus produced. Next, the ultrasonic disintegration is carried out as follows: with the probe immersed over a length of 4 cm, the output power is adjusted so as to obtain a deflection of the needle of the power dial indicating 20%. The disintegration is carried out for 420 seconds. Next, the particle size measurement is taken after a known volume (expressed in ml) of the homogenized suspension has been introduced into the container of the particle size analyser.

The value of the median diameter $Ø_{50S}$ (or Sympatec median diameter) that is obtained is smaller the higher the disintegratability of the silica. It is also possible to determine the (10×volume of suspension (in ml) introduced)/(optical density of the suspension detected by the particle size analyser) ratio may also be determined (this optical density is around 20). This ratio is indicative of the content of particles of a size of less than 0.1 μm, which particles are not detected by the particle size analyser. This ratio is called the ultrasonic Sympatec disintegration factor ($F_{DS}$).

Another disintegration test is carried out according to the following protocol:

The cohesion of the agglomerates is assessed by a particle size measurement (using laser diffraction) carried out on a suspension of silica ultrasonically disintegrated beforehand; in this way, the disintegrability of the silica (break-up of objects from 0.1 to a few tens of microns) is measured. The ultrasonic disintegration is carried out using a Bioblock VIBRACELL sonifier (600 W), used at 80% of maximum power, fitted with a 19 mm diameter probe. The particle size measurement is carried out by laser diffraction on a Malvern Mastersizer 2000 particle size analyser.

1 gram of silica is weighed in a pillbox (height: 6 cm and diameter: 4 cm) and deionized water is added to bring the weight to 50 grams: an aqueous suspension containing 2% silica, which is homogenized for 2 minutes by magnetic stirring, is thus produced. Ultrasonic disintegration is then carried out for 420 seconds. Next, the particle size measurement is taken after all of the homogenized suspension has been introduced into the container of the particle size analyser.

The value of the median diameter $Ø_{50M}$ (or Malvern median diameter) that is obtained is smaller the higher the disintegratability of the silica. It is also possible to determine the (10×blue laser obscuration value)/(red laser obscuration value) ratio. This ratio is indicative of the content of particles smaller in size than 0.1 μm. This ratio is called the Malvern ultrasonic disintegration factor ($F_{DM}$).

A disintegration rate, denoted α, may be measured by means of another ultrasonic disintegration test, at 100% power of a 600 watt probe, operating in pulsed mode (i.e.: on for 1 second/off for 1 second) so as to prevent the ultrasonic probe from heating up excessively during the measurement. This known test, forming the subject matter for example of Application WO 99/28376 (see also Applications WO 99/28380, WO 00/73372 and WO 00/73373), allows the variation in the volume-average size of the particle agglomerates to be continuously measured during sonification, according to the indications given below. The set-up used consists of a laser particle size analyser (of the MASTERSIZER S type sold by Malvern Instruments: He—Ne laser source emitting in the red at a wavelength of 632.8 nm) and of its preparation station (Malvern Small Sample Unit MSX1), between which a continuous flux stream treatment cell (Bioblock M72410) fitted with an ultrasonic probe (600 watt VIBRACELL-type 12.7 mm sonifier sold by Bioblock) was inserted. A small quantity (150 mg) of silica to be analysed is introduced with 160 ml of water into the preparation station, the rate of circulation being set at its maximum. At least three consecutive measurements are carried out in order to determine, using the known Fraunhofer calculation method (Malvern 3$$D calculation matrix), the initial volume-average diameter of the agglomerates, denoted $d_v[0]$. Sonification (pulsed mode: on for 1 s/off for 1 s) is then applied at 100% power (i.e. 100% of the maximum position of the tip amplitude) and the variation in the volume-average diameter $d_v[t]$ as a function of time t is monitored for about 8 minutes, a measurement being taken approximately every 10 seconds. After an induction period (about 3-4 minutes), it is observed that the inverse of the volume-average diameter $1/d_v[t]$ varies linearly, or substantially linearly, with time t (disintegration steady state). The rate of disintegration α is calculated by linear regression from the curve of variation of $1/d_v[t]$ as a function of time t in the disintegration steady state region (in general, between 4 and 8 minutes approximately); it is expressed in $\mu m^{-1} \cdot min^{-1}$.

The aforementioned Application WO 99/28376 describes in detail a measurement device that can be used for carrying out this ultrasonic disintegration test. This device consists of a closed circuit in which a stream of particle agglomerates in suspension in a liquid can circulate. This device essentially comprises a specimen preparation station, a laser particle size analyser and a treatment cell. Setting to atmospheric pressure, within the specimen preparation station and the actual treatment cell, makes it possible for the air bubbles that form during sonification (i.e. the action of the ultrasonic probe) to be continuously removed. The specimen preparation station (Malvern Small Sample Unit MSX1) is designed to receive the silica specimen to be tested (in suspension in the liquid) and to make it circulate around the circuit at the preset speed (potentiometer-maximum speed about 3 l/min) in the form of a stream of liquid suspension. This preparation station simply consists of a receiving container which contains the suspension to be analysed and through which the said suspension flows. It is equipped with a variable-speed stirring motor so as to prevent any sedimentation of the particle agglomerates of the suspension, a centrifuge mini-pump is designed to circulate the suspension in the circuit; the inlet of the preparation station is connected to the open air via an opening intended to receive the charge specimen to be tested and/or the liquid used for the suspension. Connected to the preparation station is a laser particle size analyser (MASTERSIZER S) whose function is to continuously measure, at regular time intervals, the volume-average size $d_v$ of the agglomerates, as the stream passes, by a measurement cell to which the recording means and the automatic calculation means of the particle size analyser are coupled. It will be briefly recalled here that laser particle size analysers make use, in a known manner, of the principle of light diffraction by solid objects in suspension in a medium whose refractive index is different from that of the solid. According to the Fraunhofer theory, there is a relationship between the size of the object and the angle of diffraction of the light (the smaller the object the larger the angle of diffraction). In practice, all that is required is to measure the quantity of diffracted light for various angles of diffraction in order to be able to determine the size distribution (by volume) of the specimen, $d_v$ corresponding to the volume-average size of this distribution $d_v = \Sigma(n_i d_i^4) / \Sigma(n_i d_i^3)$ where $n_i$ is the number of objects of the class of size or diameter $d_i$). Finally, a treatment cell fitted with an ultrasonic probe is inserted between the preparation station and the laser particle size analyser, the said cell being able to operate in continuous or pulsed mode and intended to continuously break up the particle agglomerates as the stream passes. This stream is thermostatically controlled by means of a cooling circuit placed, within the cell, in a jacket surrounding the probe, the temperature being controlled, for example, by a temperature probe immersed in the liquid within the preparation station.

The Sears number is determined using the method described by G. W. Sears in the article in Analytical Chemistry, Vol. 28, No. 12, December 1956 entitled "*Determination of specific surface area of colloidal silica by titration with sodium hydroxide*".

The Sears number is the volume of 0.1M sodium hydroxide solution needed to raise the pH of a 10 g/l silica suspension in a 200 g/l sodium chloride medium from 4 to 9.

To do this, 400 grams of sodium chloride are used to prepare a 200 g/l sodium chloride solution acidified to pH 3 with a 1M hydrochloric acid solution. The weighings are performed by means of a Mettler precision balance. 150 ml of this sodium chloride solution are delicately added to a 250 ml beaker into which a mass M (in g) of the specimen to be analysed, corresponding to 1.5 grams of dry silica, has been introduced beforehand. Ultrasound is applied for 8 minutes to the dispersion obtained (Branson 1500 W ultrasonic probe; 60% amplitude, 13 mm diameter), the beaker being in an ice-filled crystallizer. The solution obtained is then homogenized by magnetic stirring, using a bar magnet having dimensions of 25 mm×5 mm. A check is made that the pH of the suspension is less than 4, if necessary by adjusting it using a 1M hydrochloric acid solution. Next, a 0.1M sodium hydroxide solution is added at a rate of 2 ml/min by means of a Metrohm titrator pH meter (672 Titroprocessor, 655 Dosimat) precalibrated using pH 7 and pH 4 buffer solutions. (The titrator pH meter was programmed as follows: 1) Call up the "Get pH" program—and 2) Introduce the following parameters: pause (wait time before the start of titration): 3 s; reactant flow rate: 2 ml/min; anticipation (adaptation of the titration rate to the slope of the pH curve): 30; stop pH: 9.40; critical EP (sensitivity of detection of the equivalence point): 3; report (parameters for printing the titration report): 2, 3 and 5 (i.e. creation of a detailed report, list of measurement points and titration curve)). The exact volumes $V_1$ and $V_2$ of sodium hydroxide solution added in order to obtain a pH of 4 and a pH of 9, respectively, are determined by interpolation. The Sears number for 1.5 grams of dry silica is equal to $((V_2-V_1) \times 150)/(SC \times M)$, where:

$V_1$: volume of 0.1M sodium hydroxide solution at $pH_1=4$;
$V_2$: volume of 0.1M sodium hydroxide solution at $pH_2=9$;
M: mass of the specimen (in g);
SC: solids content (in %).

The pore distribution width may possibly be also illustrated by the parameter W/FI determined by mercury porosimetry. The measurement is carried out using PASCAL 140 and PASCAL 440 porosimeters sold by ThermoFinnigan, operating in the following manner: a quantity of specimen between 50 and 500 mg (in the present case 140 mg) is introduced into a measurement cell. This measurement cell is installed in the measurement unit of the PASCAL-140 apparatus. The specimen is then vacuum-degassed for the time needed to achieve a pressure of 0.01 kPa (typically around 10 minutes). The measurement cell is then filled with mercury. The first part of the mercury intrusion curve Vp=f(P), where Vp is the mercury intrusion volume and P is the applied pressure, for pressures of less than 400 kPa, is determined using the PASCAL 140 porosimeter. The measurement cell is then installed in the measurement unit of the PASCAL 440 porosimeter, the second part of the mercury intrusion curve Vp=f(P) for pressures between 100 kPa and 400 MPa being determined using the PASCAL 440 porosimeter. The porosimeters are used in PASCAL mode so as to permanently adjust the rate of mercury intrusion according to the variations in the intrusion volume. The rate parameter in PASCAL mode is set to 5. The pore radii Rp are calculated from the pressure values P using the Washburn equation, assuming that the pores are cylindrical, choosing a contact angle θ of 140° and a surface tension γ of 480 dynes/cm (or N/m). The pore volumes Vp are relative to the mass of silica introduced and are expressed in cm³/g. The signal Vp=f(Rp) is smoothed by combining a logarithmic filter ("smooth dumping factor" filter parameter F=0.96) and a moving-average filter ("number of points to average" filter parameter f=20). The pore size distribution is obtained by calculating the derivative dVp/dRp of the smooth intrusion curve. The fineness index FI is the pore radius value (expressed in ångströms) corresponding to the maximum of the pore size distribution dVp/dRp. The mid-height width of the pore size distribution dVp/dRp is denoted by W.

The number of silanols per nm² of surface area is determined by grafting methanol onto the surface of the silica. Firstly, 1 gram of raw silica is put into suspension in 10 ml of methanol, in a 110 ml autoclave (Top Industrie, reference 09990009). A bar magnet is introduced and the autoclave, hermetically sealed and thermally insulated, is heated to 200° C. (40 bar) on a magnetic stirrer, heating for 4 hours. The autoclave is then cooled in a cold water bath. The grafted silica is recovered by settling and the residual methanol is evaporated in a stream of nitrogen. Finally, the grafted silica is vacuum dried for 12 hours at 130° C. The carbon content is determined by an elemental analyser (NCS 2500 analyser from CE Instruments) on the raw silica and on the grafted silica. This quantitative determination is carried out on the grafted silica within the three days following the end of drying—this is because the humidity of the air or heat may cause hydrolysis of the methanol grafting. The number of silanols per nm² is then calculated using the following formula:

$$N_{SiOH/nm^2}=[(\%C_g-\%C_r)\times 6.023\times 10^{23}]/[S_{BET}\times 10^{18}\times 12\times 100]$$

where % $C_g$: percent mass of carbon present on the grafted silica;

% $C_r$: percent mass of carbon present on the raw silica;

$S_{BET}$: BET specific surface area of silica (in m²/g).

According to a first variant of the invention, a novel silica will now be proposed which is characterized in that it possesses:

a CTAB specific surface area ($S_{CTAB}$) of between 40 and 525 m²/g;

a BET specific surface area ($S_{BET}$) of between 45 and 550 m²/g;

a size distribution width $L_d$ ((d84−d16)/d50) of objects measured by XDC particle size analysis after ultrasonic disintegration of at least 0.91, in particular at least 0.94, and a pore volume distribution as a function of the size of the pores such that the ratio $V_{(d5-d50)}/V_{(d5-d100)}$ is at least 0.66, in particular at least 0.68.

The silica according to this variant of the invention possesses, for example:

a size distribution width $L_d$ ((d84−d16)/d50) of objects measured by XDC particle size analysis after ultrasonic disintegration of at least 1.04; and a pore volume distribution as a function of the size of the pores such that the ratio $V_{(d5-d50)}/V_{(d5-d100)}$ is at least 0.71.

This silica may have a ratio $V_{(d5-d50)}/V_{(d5-d100)}$ of at least 0.73, in particular at least 0.74. This ratio may be at least 0.78, especially at least 0.80 or even at least 0.84.

A second variant of the invention consists of a novel silica characterized in that it possesses:

a CTAB specific surface area ($S_{CTAB}$) of between 40 and 525 m²/g;

a BET specific surface area ($S_{BET}$) of between 45 and 550 m²/g; and a pore distribution width ldp of greater than 0.70, in particular greater than 0.80, especially greater than 0.85.

This silica may have a pore distribution width ldp of greater than 1.05, for example greater than 1.25 or even greater than 1.40.

The silica according to this variant of the invention preferably possesses a size distribution width $L_d$ ((d84−d16)/d50) of objects measured by XDC particle size analysis after ultrasonic disintegration, of at least 0.91, in particular at least 0.94, for example at least 1.0.

Also proposed, according to a third variant of the invention, is a novel silica characterized in that it possesses:

a CTAB specific surface area ($S_{CTAB}$) of between 40 and 525 m²/g;

a BET specific surface area ($S_{BET}$) of between 45 and 550 m²/g;

a size distribution width $L'_d$ ((d84−d16)/d50) of objects smaller than 500 nm, measured by XDC particle size analysis after ultrasonic disintegration, of at least 0.95; and a pore volume distribution as a function of the size of the pores such that the ratio $V_{(d5-d50)}/V_{(d5-d100)}$ is at least 0.71.

This silica may have a ratio $V_{(d5-d50)}/V_{(d5-d100)}$ of at least 0.73, in particular at least 0.74. This ratio may be at least 0.78, especially at least 0.80 or even at least 0.84.

A fourth variant of the invention consists of a novel silica characterized in that it possesses:

a CTAB specific surface area ($S_{CTAB}$) of between 40 and 525 m²/g;

a BET specific surface area ($S_{BET}$) of between 45 and 550 m²/g;

a size distribution width $L_d$ ((d84−d16)/d50) of objects smaller than 500 nm, measured by XDC particle size analysis after ultrasonic disintegration, of at least 0.90, in particular at least 0.92; and a pore volume distribution as a function of 25 the size of the pores such that the ratio $V_{(d5-d50)}/V_{(d5-d100)}$ is at least 0.74.

This silica may have a ratio $V_{(d5-d50)}/V_{(d5-d100)}$ of at least 0.78, especially at least 0.80 or even at least 0.84.

In the silicas according to the invention (that is to say those in accordance with one of the four variants of the invention), the pore volume provided by the coarsest pores usually represents the largest proportion of the structure.

The silicas may have both an object size distribution width $L_d$ of at least one 1.04 and an object size (smaller than 500 nm) distribution width $L'_d$ of at least 0.95.

The size distribution width $L_d$ of objects of the silicas according to the invention may in certain cases be at least 1.10, in particular at least 1.20; it may be at least 1.30, for example at least 1.50 or even at least 1.60.

Likewise, the object size (smaller than 500 nm) distribution $L'_d$ of the silicas according to the invention may be, for example, at least 1.0, in particular at least 1.10 and especially at least 1.20.

Preferably, the silicas according to the invention possess a particular surface chemistry such that they have a (Sears number×1000)/(BET specific surface area ($S_{BET}$)) ratio of less than 60, preferably less than 55, for example less than 50.

The silicas according to the invention generally have a high, and therefore a typical object size which may be such that the mode of their particle size distribution measured by XDC particle size analysis after ultrasonic disintegration (in water) satisfies the condition: XDC mode (nm)≥(5320/$S_{CTAB}$ (m²/g))+8, or even the condition: XDC mode (in nm)≥(5320/$S_{CTAB}$ (m²/g))+10.

The silicas according to the invention may possess, for example, a pore volume ($V_{80}$) formed by the pores having diameters between 3.7 and 80 nm of at least 1.35 cm³/g, in particular at least 1.40 cm³/g or even at least 1.50 cm³/g.

The silicas according to the invention preferably have a satisfactory dispersibility in polymers.

Their median diameter ($Ø_{50S}$), after ultrasonic disintegration, is in general less than 8.5 μm; it may be less than 6.0 μm, for example less than 5.5 μm.

Likewise, their median diameter ($Ø_{50M}$), after ultrasonic disintegration, is in general less than 8.5 μm, it may be less than 6.0 μm for example less than 5.5 μm.

They may also possess a rate of disintegration, denoted by α, measured in the test referred to previously as ultrasonic disintegration in pulsed mode, at 100% power of a 600 watt probe, of at least 0.0035 μm⁻¹·min⁻¹, in particular at least 0.0037 μm-1 min⁻¹.

The silicas according to the invention may have an ultrasonic disintegration factor ($F_{DS}$) of greater than 3 ml, in particular greater than 3.5 ml, especially greater than 4.5 ml.

Their ultrasonic disintegration factor ($F_{DM}$) may be greater than 6, in particular greater than 7, especially greater than 11.

The silicas according to the present invention may have a weight-average particle size, measured by XDC particle size analysis after ultrasonic disintegration, $d_w$, of between 20 and 300 nm, especially between 30 and 300 nm, for example between 40 and 160 nm.

In general, the silicas according to the present invention also have at least one, or even all, of the following three characteristics:

a particle size distribution such that $d_w \geq (16{,}500\ \text{nm·m}^2/\text{g}/S_{CTAB}) - 30$ nm a porosity such that W/FI ≥ −0.0025 g/m² SCTAB+0.85 a number of silanols per unit area, $N_{SiOH/nm^2}$, such that $N_{SiOH/nm^2} = -0.027\ g/m^2\ S_{CTAB} + 10.5$ According to one embodiment, the silicas according to the invention generally have:

a CTAB specific surface area ($S_{CTAB}$) of between 60 and 330 m²/g, in particular between 80 and 290 m²/g;

a BET specific surface area ($S_{BET}$) of between 70 and 350 m²/g, in particular between 90 and 320 m²/g.

Their CTAB specific surface area may be between 90 and 230 m²/g, especially between 95 and 200 m²/g, for example between 120 and 190 m²/g.

Likewise, their BET specific surface area may be between 110 and 270 m²/g, especially between 115 and 250 m²/g, for example between 135 and 235 m²/g.

According to another embodiment, the silicas according to the invention generally have:

a CTAB specific surface area of between 40 and 380 m²/g, in particular between 45 and 280 m²/g; and a BET specific surface area of between 45 and 400 m²/g, in particular between 50 and 300 m²/g.

Their CTAB specific surface area may be between 115 and 260 m²/g, especially between 145 and 260 m²/g.

Likewise, their BET specific surface area may be between 120 and 280 m²/g, especially between 150 and 280 m²/g.

The silicas according to the present invention may have a certain microporosity; thus, the silicas according to the invention usually are such that ($S_{BET} - S_{CTAB}$) ≥ 5 m²/g, in particular ≥ 15 m²/g, for example ≥ 25 m²/g.

This microporosity is not in general too great: the silicas according to the invention are generally such that ($S_{BET} - S_{CTAB}$) < 50 m²/g, preferably < 40 m²/g.

The pH of the silicas according to the invention is usually between 6.3 and 7.8, especially between 6.6 and 7.5.

They possess a DOP oil uptake that varies, usually, between 220 and 330 ml/100 g, for example between 240 and 300 ml/100 g.

They may be in the form of approximately spherical beads with a mean size of at least 80 μm.

This mean size of the beads may be at least 100 μm, for example at least 150 μm; it is in general at most 300 μm and preferably lies between 100 and 270 μm. This mean size is determined according to the NF X 11507 (December 1970) standard by dry screening and determination of the diameter corresponding to a cumulative oversize of 50%.

The silicas according to the invention may also be in the form of powder having a mean size of at least 15 μm; for example, it is between 15 and 60 μm (especially between 20 and 45 μm) or between 30 and 150 μm (especially between 45 and 120 μm).

They may also be in the form of granules having a size of at least 1 mm, in particular between 1 and 10 mm, along the axis of their largest dimension (length).

The silicas according to the invention are preferably prepared by the preparation process according to the invention and described above.

The silicas according to the invention or those prepared by the process according to the invention find particularly useful application in the reinforcement of natural or synthetic polymers.

The polymer compositions in which they are used, especially as reinforcing filler, are in general based on one or more polymers or copolymers, in particular one or more elastomers, especially thermoplastic elastomers, preferably having at least one glass transition temperature between −150 and +300° C., for example between −150 and +20° C.

As possible polymers, mention may be made of diene polymers, in particular diene elastomers.

For example, it is possible to use polymers or copolymers derived from aliphatic or aromatic monomers comprising at least one unsaturated group (such as especially ethylene, propylene, butadiene, isoprene and styrene), polybutyl acrylate, or blends thereof; mention may also be made of silicone elastomers, functionalized elastomers (for example those functionalized by functional groups capable of reacting with the surface of the silica) and halogenated polymers. Polyamides may be mentioned.

The polymer (or copolymer) may be a bulk polymer (or copolymer), a polymer (or copolymer) latex or a solution of a polymer (or copolymer) in water or in any other suitable dispersing liquid.

As diene elastomers, mention may be made, for example, of polybutadienes (BR), polyisoprenes (IR), butadiene copolymers, isoprene copolymers, or blends thereof, and in particular styrene-butadiene copolymers (SBR, especially emulsion styrene-butadiene copolymers ESBR or solution styrene-butadiene copolymers SSBR), isoprene-butadiene copolymers (BIR), isoprene-styrene copolymers (SIR), styrene-butadiene-isoprene copolymers (SBIR) and ethylene-propylene-diene terpolymers (EPDM).

Mention may also be made of natural rubber (NR).

The polymer compositions may be sulphur-vulcanized (vulcanisates are then obtained) or crosslinked, especially by peroxides.

In general, the polymer compositions furthermore include at least one coupling (silica/polymer) agent and/or at least one covering agent; they may also include inter alia an antioxidant.

It is possible in particular to use, as coupling agents, what are called "symmetrical" or "asymmetrical", polysulphide-based silanes, these being given as non-limiting examples;

mention may more particularly be made of bis((C$_1$-C$_4$)alkoxyl-(C$_1$-C$_4$)alkylsilyl(C$_1$-C$_4$)alkyl polysulphides (especially disulphides, trisulphides or tetrasulphides) such as, for example, bis(3-(trimethoxysilyl)propyl)polysulphides or bis (3-(triethoxysilyl)propyl)polysulphides. Mention may also be made of monoethoxydimethylsilylpropyl tetrasulphide.

The coupling agent may be pregrafted onto the polymer.

It may also be employed in the free state (that is to say not pregrafted) or grafted onto the surface of the silica. The same applies to the optional covering agent.

The use of a silica according to the invention or a silica prepared by the process according to the invention may allow the quantity of coupling agent to be employed in reinforced polymer compositions to be substantially reduced, for example by around 20%, while maintaining a substantially identical compromise of properties.

The coupling agent may optionally be combined with a suitable "coupling activator", that is to say a compound which, when mixed with this coupling agent, increases the effectiveness of the latter.

The proportion by weight of silica in the polymer composition may vary over quite a wide range. Usually it represents from 20 to 80%, for example 30 to 70%, of the quantity of polymer(s).

The silica according to the invention may advantageously constitute all of the inorganic reinforcing filler, and even all of the reinforcing filler, of the polymer composition.

However, at least one other reinforcing filler, such as in particular a commercial highly dispersible silica such as, for example, Z1165 MP or Z1115MP, a treated precipitated silica (for example one "doped" using a cation such as aluminium), or another inorganic reinforcing filler such as, for example, alumina, or even an organic reinforcing filler, especially carbon black (optionally covered with an inorganic layer, for example with silica), may optionally be combined with this silica according to the invention. The silica according to the invention therefore preferably constitutes at least 50%, or even at least 80%, by weight of all of the reinforcing filler.

Mention may be made, as non-limiting examples, of finished articles based on the polymer compositions described above (especially those based on the above-mentioned vulcanisates), shoe soles (preferably in the presence of a coupling (silica/polymer) agent), floor coverings, gas barriers, fire-retarding materials and also engineering components such as cable car wheels, seals for domestic electrical appliances, seals for liquid or gas pipes, seals for brake systems, sheaths or ducts, cables and drive belts.

In the case of shoe soles, it is possible to use, advantageously in the presence of a coupling (silica/polymer) agent, polymer compositions based, for example, on natural rubber (NR), polyisoprene (IR), polybutadiene (BR), styrene-butadiene copolymer (SBR) and butadiene-acryonitrile copolymer (NBR).

For the engineering components, it is possible to use, for example in the presence of a coupling (silica/polymer) agent, polymer compositions based, for example, on natural rubber (NR), polyisoprene (IR), polybutadiene (BR), styrene-butadiene copolymer (SBR), polychloroprene, butadiene-acrylonitrile copolymer (NBR), hydrogenated or carboxylated nitrile rubber, isobutylene-isoprene copolymer (IIR), halogenated (especially brominated or chlorinated) butyl rubber, ethylene-propylene copolymer (EPM), ethylene-propylene-diene terpolymer (EPDM), chlorinated polyethylene, chlorosulphonated polyethylene, epichlorohydrin rubber, silicones, fluorocarbon rubber and polyacrylates.

The silicas according to the invention or those prepared by the process according to the invention may also be employed as a catalyst support, as an absorbent for active materials (in particular a support for liquids, for example those used in food, such as vitamins (vitamin E), choline chloride), as a viscosity-modifying, texturing or anti-clumping agent, as an element for battery separators, or as an additive for dentrifices or for paper.

The following examples illustrate the invention without, however, limiting the scope thereof.

Example 1

10 litres of purified water were introduced into a 25 litre stainless steel reactor. The solution was heated to 80° C. The entire reaction was carried out at this temperature. 80 g/l of sulphuric acid were introduced, with stirring (350 rpm, propeller stirrer), until the pH reached a value of 4.

Simultaneously introduced into the reactor over 35 minutes were a sodium silicate solution (having an SiO$_2$/Na$_2$O weight ratio of 3.52) having a concentration of 230 g/l at a rate of 76 g/min and sulphuric acid, having a concentration of 80 g/l, at a rate set so as to maintain the pH of the reaction mixture at a value of 4. After the 30th minute of addition, the stirring rate was increased to 450 rpm.

At the end of 35 minutes of simultaneous addition, the introduction of acid was stopped when the pH reached a value of 9. The flow of silicate was then also stopped. The mixture was then matured for 15 minutes at pH 9. At the end of maturing, the stirring rate was reduced to 350 rpm.

Next, the pH was taken to pH 8 by introducing sulphuric acid. A new simultaneous addition was carried out for 40 minutes with a sodium silicate flow rate of 76 g/min (the same sodium silicate as in the case of the first simultaneous addition) and a flow rate of sulphuric acid, with a concentration of 80 g/l, regulated so as to maintain the pH of the reaction mixture at a value of 8.

After this simultaneous addition, the reaction mixture is taken to a pH of 4 by sulphuric acid having a concentration of 80 g/l. The mixture is matured for 10 minutes at pH 4. 250 ml of flocculant FA 10 (polyoxyethylene having a molar mass of $5 \times 10^6$ g) at 1% were introduced after the 3rd minute of the maturing.

The slurry was filtered and washed under vacuum (16.7% solids content). After dilution (13% solids content), the cake obtained was mechanically broken up. The resulting slurry was spray dried by means of a turbine spray dryer.

The characteristics of the silica P1 obtained were then the following:
CTAB specific surface area: 221 m$^2$/g;
BET specific surface area: 240 m$^2$/g;
$V_{(d5-d50)}/V_{(d5-d100)}$: 0.74;
Width $L_d$ (XDC): 1.62;
Pore distribution width ldp: 1.42;
Width $L'_d$ (XDC): 1.27;
Sears number×1000/BET specific surface area: 42.9;
XDC mode: 39 nm;
Pore volume $V_{80}$: 1.69 cm.$^3$/g;
$\emptyset_{50S}$ (after ultrasonic disintegration): 4.8 μm;
$F_{DS}$: 4.6 ml;
α: 0.00626 μm$^1$.min$^{-1}$;
$d_w$: 79 nm;
W/FI: 0.62;
$N_{SiOH/nm}{}^2$: 3.90.

Example 2

9.575 kg of purified water and 522 g of sodium silicate (SiO$_2$/Na$_2$O weight ratio of 3.55) with a concentration of 235 g/l were introduced into a 25 litre stainless steel reactor. The solution was heated to 80° C. The entire reaction was carried out at this temperature. Sulphuric acid, with a concentration of 80 g/l, was introduced, with stirring (300 rpm, propeller stirrer), until the pH reached a value of 4 (615 g of acid introduced).

Simultaneously introduced into the reactor over 40 minutes were a sodium silicate solution (having an $SiO_2/Na_2O$ weight ratio of 3.55) having a concentration of 235 g/l at a rate of 50 g/min and sulphuric acid, having a concentration of 80 g/l, at a rate set so as to maintain the pH of the reaction mixture at a value of 4.

At the end of 40 minutes of simultaneous addition, the introduction of acid was stopped when the pH reached a value of 9. The flow of silicate was then also stopped. The mixture was then matured for 15 minutes at pH 9 at 80° C.

Next, the pH was taken to pH 8 by introducing sulphuric acid over 2 minutes. A new simultaneous addition was carried out for 60 minutes with a sodium silicate flow rate of 76 g/min (the same sodium silicate as in the case of the first simultaneous addition) and a flow rate of sulphuric acid, with a concentration of 80 g/l, regulated so as to maintain the pH of the reaction mixture at a value of 8.

After this simultaneous addition, the reaction mixture is taken to a pH of 4 over 5 minutes by sulphuric acid having a concentration of 80 g/l. The mixture is matured for 10 minutes at pH 4.

The slurry was filtered and washed under vacuum (5.5% cake solids content). After dilution (12% solids content), the cake obtained was mechanically broken up. The resulting slurry was spray dried by means of a turbine spray dryer.

The characteristics of the silica P2 obtained were then the following:
CTAB specific surface area: 182 m²/g;
BET specific surface area: 197 m²/g;
$V_{(d5-d50)}/V_{(d5-d100)}$: 0.76;
Width $L'_d$ (XDC): 1.12;
Pore distribution width ldp: 1.26;
Width $L'_d$ (XDC): 0.90;
XDC mode: 57 nm;
Pore volume $V_{80}$: 1.40 cm³/g;
$Ø_{50S}$ (after ultrasonic disintegration): 4.1 μm,
$F_{DS}$: 4.0 ml Example 3

10 litres of sodium silicate ($SiO_2/Na_2O$ weight ratio of 3.55) with a concentration of 10 g/l were introduced into a 25 litre stainless steel reactor. The solution was heated to 80° C. The entire reaction was carried out at this temperature. Sulphuric acid, with a concentration of 80 g/l, was introduced, with stirring (300 rpm, propeller stirrer), until the pH reached a value of 4 (615 g of acid introduced).

Simultaneously introduced into the reactor over 40 minutes were a sodium silicate solution (having an $SiO_2/Na_2O$ weight ratio of 3.55) having a concentration of 230 g/l at a rate of 50 g/min and sulphuric acid, having a concentration of 80 g/l, at a rate set so as to maintain the pH of the reaction mixture at a value of 4.

At the end of 40 minutes of simultaneous addition, the introduction of acid was stopped when a pH of 8 was reached.

A new simultaneous addition was carried out for 60 minutes with a sodium silicate flow rate of 50 g/min (the same sodium silicate as in the case of the first simultaneous addition) and a flow rate of sulphuric acid, with a concentration of 80 g/l, set so as to maintain the pH of the reaction mixture at a value of 8.

After this simultaneous addition, the reaction mixture is taken to a pH of 4 over 4 minutes by sulphuric acid having a concentration of 80 g/l. The mixture is matured for 10 minutes at pH 4.

The slurry was filtered and washed under vacuum (13.7% cake solids content). After dilution (11.2% solids content), the cake obtained was mechanically broken up. The resulting slurry was spray dried by means of a turbine spray dryer.

The characteristics of the silica P3 were then the following:
CTAB specific surface area: 228 m²/g;
BET specific surface area: 245 m²/g;
$V_{(d5-d50)}/V_{(d5-d100)}$: 0.76;
Width $L_d$ (XDC): 1.48;
Pore distribution width ldp: 1.98;
Width $L'_d$ (XDC): 1.16;
XDC mode: 42 nm;
Pore volume $V_{80}$: 1.48 cm³/g;
$Ø_{50S}$ (after ultrasonic disintegration): 4.4 μm;
$F_{DS}$: 4.3 ml.

Example 4

12 litres of a sodium silicate solution ($SiO_2/Na_2O$ weight ratio of 3.5) with a concentration of 10 g/l were introduced into a 25 litre stainless steel reactor. The solution was heated to 80° C. The entire reaction was carried out at this temperature. Sulphuric acid, with a concentration of 80 g/l, was introduced, with stirring (300 rpm, propeller stirrer), until the pH reached a value of 8.9.

Simultaneously introduced into the reactor over 15 minutes were a sodium silicate solution (having an $SiO_2/Na_2O$ weight ratio of 3.5) having a concentration of 230 g/l at a rate of 76 g/min and sulphuric acid, having a concentration of 80 g/l, at a rate set so as to maintain the pH of the reaction mixture at a value of 8.9. Thus, a sol of scarcely aggregated particles was obtained. The sol was withdrawn and rapidly cooled using a copper coil through which cold water circulates. The reactor was rapidly cleaned.

4 litres of purified water were introduced into the 25 litre reactor. Sulphuric acid, having a concentration of 80 g/l, was introduced until the pH reached a value of 4. A simultaneous addition of the cold sol with a flow rate of 195 g/min and sulphuric acid, having a concentration of 80 g/l, with a flow rate allowing the pH to be set to 4, was carried out over 40 minutes. A maturing step lasting 10 minutes was carried out.

After 40 minutes of simultaneous sol/sulphuric acid addition, there was a simultaneous addition, over 20 minutes, of sodium silicate with a flow rate of 76 g/min (the same sodium silicate as in the case of the first simultaneous addition) and sulphuric acid with a flow rate of 80 g/l set so as to maintain the pH of the reaction mixture at a value of 4. After the 20 minutes, the flow of acid was stopped when a pH of 8 was obtained.

A new simultaneous addition was carried out for 60 minutes with a sodium silicate flow rate of 76 g/min (the same sodium silicate as in the case of the first simultaneous addition) and a flow rate of sulphuric acid, with a concentration of 80 g/l, set so as to maintain the pH of the reaction mixture at a value of 8. The stirring rate was increased when the mixture became very viscous.

After this simultaneous addition, the reaction mixture is taken to a pH of 4 over 5 minutes by sulphuric acid having a concentration of 80 g/l. The mixture is matured for 10 minutes at pH 4.

The slurry was filtered and washed under vacuum (15% cake solids content). After dilution, the cake obtained was mechanically broken up. The resulting slurry was spray dried by means of a turbine spray dryer.

The characteristics of the silica P4 were then the following:
CTAB specific surface area: 230 m²/g;
BET specific surface area: 236 m²/g;
$V_{(d5-d50)}/V_{(d5-d100)}$: 0.73;
Width $L_d$ (XDC): 1.38;
Pore distribution width ldp: 0.67;
Width. $L'_d$ (XDC): 1.14;
XDC mode: 34 nm;
Pore volume $V_{80}$: 1.42 cm³/g;
$Ø_{50S}$ (after ultrasonic disintegration): 3.8 µm;
$F_{DS}$: 4.6 ml.

Example 5

10 litres of a sodium silicate solution (SiO₂/Na₂O weight ratio of 3.48) with a concentration of 5 g/l were introduced into a 25 litre stainless steel reactor. The solution was heated to 80° C. Sulphuric acid, with a concentration of 80 g/l, was introduced, with stirring (300 rpm, propeller stirrer), until the pH reached a value of 4.2.

Simultaneously introduced into the reactor over 30 minutes were a sodium silicate solution (having an SiO₂/Na₂O weight ratio of 3.48) having a concentration of 230 g/l at a rate of 75 g/min and sulphuric acid, having a concentration of 80 g/l, at a rate set so as to maintain the pH of the reaction mixture at a value of 4.2.

After 30 minutes of simultaneous addition, the introduction of acid was stopped when the pH reached a value of 9. The flow of silicate was then also stopped. A maturing step was carried out for 15 minutes at pH 9, while progressively increasing the temperature (over 15 minutes) from 80 to 90° C., at which value the rest of the reaction was carried out.

Next, the pH was brought to pH 8 by introducing sulphuric acid having a concentration of 80 g/l. There was then a new simultaneous addition, carried out over 50 minutes, of sodium silicate at a rate of 76 g/min (the same sodium silicate as in the first simultaneous addition) and of sulphuric acid, with a concentration of 80 g/l, at a rate set so as to maintain the pH of the reaction mixture at a value of 8.

After this simultaneous addition, the reaction mixture is taken to a pH of 4 by sulphuric acid having a concentration of 80 g/l. The mixture is matured for 10 minutes at pH 4.

The slurry was filtered and washed under vacuum (19.6% cake solids content). After dilution (10% solids content), the cake obtained was mechanically broken up. The resulting slurry was spray dried by means of a turbine spray dryer.

The characteristics of the silica P5 obtained were then the following:
CTAB specific surface area: 135 m²/g;
BET specific surface area: 144 m²/g;
$V_{(d5-d50)}/V_{(d5-d100)}$: 0.76;
Width $L_d$ (XDC): 1.52;
Pore distribution width ldp: 2.65;
Width $L'_d$ (XDC): 0.92;
Sears number×1000/BET specific surface area: 49.3;
XDC mode: 57 nm;
Pore volume $V_{80}$: 1.12 cm³/g;
$Ø_{50S}$ (after ultrasonic disintegration): 5.9 µm;
$d_w$: 159 nm;
W/FI: 1.47;
$N_{SiOH/nm^2}$: 5.20.

Example 6

Three polymer compositions were prepared:
one containing highly dispersible precipitated silica Z1165MP, sold by Rhodia, having a density of 2.1 g/cm³, and a coupling agent (reference composition R1);
the other two each containing silica prepared in Example 4 and a coupling agent (compositions C1 and C2).

Silica Z1165MP had the following characteristics:
CTAB specific surface area: 160 m²/g;
Width $L_d$ (XDC): 0.56; Pore distribution width ldp: 0.50;
Width $L'_d$ (XDC): 0.56;
XDC mode: 41 nm;
Pore volume $V_{80}$ 1.12 cm³/g;
$Ø_{50S}$ (after ultrasonic disintegration)<6 µm;
α.: 0.0049 .µm⁻¹min⁻¹;
$d_w$: 59 nm;
W/FI: 0.39;
$N_{SiOH/nm^2}$: 8.10.

TABLE 1

(compositions in parts by weight)

| | Composition R1 | Composition C1 | Composition C2 |
|---|---|---|---|
| SBR[1] | 100 | 100 | 100 |
| Silica Z1165MP | 50 | 0 | 0 |
| Silica of Example 4 | 0 | 50 | 50 |
| Silane Si69[2] | 4 | 4 | 6.25 |
| Diphenylguanidine | 1.45 | 1.45 | 1.45 |
| Stearic acid | 1.1 | 1.1 | 1.1 |
| Zinc oxide | 1.82 | 1.82 | 1.82 |
| Antioxidant[3] | 1.45 | 1.45 | 1.45 |
| Sulphenamide[4] | 1.3 | 1.3 | 1.3 |
| Sulphur | 1.1 | 1.1 | 1.1 |

[1]Solution-synthesized styrene-butadiene copolymer (BUNA VSL 5525-0 type) not oil-extended;
[2]Filler/polymer coupling agent (sold by Degussa);
[3]N-(1,3-dimethylbutyl)-N'-phenyl-p-phenylenediamine;
[4]N-cyclohexyl-2-benzothiazyl sulphenamide (CBS).

Composition C1 contained a quantity of coupling agent identical to that of reference composition R1. Composition C2 contained an optimized quantity of coupling agent with regard to the specific surface area of the silica used (Example 4).

The compositions were prepared by thermomechanically working the elastomers in an internal mixer (of the Brabender type) having a volume of 75 cm³, in two steps, with a mean blade speed of 50 revolutions/minute until a temperature of 120° C. was obtained, these steps being followed by a finishing step carried out on an external mixer.

The vulcanization temperature was chosen to be 170° C. The vulcanization conditions for the compositions were tailored to the vulcanization rates of the corresponding compounds.

The properties of the compositions are given below, the measurements having been carried out (on the vulcanized compositions) according to the following standards and/or methods:

Vulcanization Properties (Rheological Properties)
(Green Properties—Rheometry at 170° C., t=30 Minutes)
NF T 43015 standard.

A Monsanto 100 S rheometer was used especially for the measurement of the minimum torque ($C_{min}$) and the maximum torque ($C_{max}$).

Ts2 corresponded to the time over which it was possible to monitor the mixture; the polymer mixture cured after Ts2 (start of vulcanization).

T90 corresponded to the time it took for the mixture to undergo 90% vulcanization.

Mechanical Properties (of the Compositions Vulcanized at 170° C.)

Tensile properties (moduli): NF T 46002 standard

The x % moduli corresponded to the stress measured at a tensile strain of x %.

TABLE 2

|  | Composition R1 | Composition C1 | Composition C2 |
|---|---|---|---|
| Vulcanization |  |  |  |
| Cmin (in · lb) | 10 | 21 | 14 |
| Ts2 (min) | 3.1 | 2.1 | 3.1 |
| T90 (min) | 29.4 | 42.0 | 36.4 |
| $C_{max}$ (in · lb) | 91 | 97.5 | 103 |
| Mechanical |  |  |  |
| 10% modulus (MPa) | 0.95 | 1.3 | 1.05 |
| 100% modulus (MPa) | 3.6 | 4.0 | 4.6 |
| 200% modulus (MPa) | 9.5 | 9.8 | 12.2 |

It may be seen that compositions C1 and C2 containing a silica according to the invention exhibit a useful compromise of properties compared with that of reference composition R1.

Despite the unoptimized vulcanization conditions, composition C1 led to a more pronounced reinforcement in terms of moduli than reference composition R1.

The adjustment in coupling agent content made in the case of composition C2 results in a vulcanization rate comparable to that of reference composition R1; in addition, composition C2 has moduli (in particular, 100% and 200% moduli) very much higher than those obtained with reference composition R1.

Example 7

10 litres of a sodium silicate solution ($SiO_2/Na_2O$ weight ratio of 3.53) with a concentration of 5 g/l were introduced into a 25 litre stainless steel reactor. The solution was heated to 80° C. Sulphuric acid, with a concentration of 80 g/l, was introduced, with stirring (300 rpm, propeller stirrer), until the pH reached a value of 4.2.

Simultaneously introduced into the reactor over 35 minutes were a sodium silicate solution (having an $SiO_2/Na_2O$ weight ratio of 3.53) having a concentration of 230 g/l at a rate of 50 g/min and sulphuric acid, having a concentration of 80 g/l, at a rate set so as to maintain the pH of the reaction mixture at a value of 4.2.

After 35 minutes of simultaneous addition, the introduction of acid was stopped when the pH reached a value of 9. The flow of silicate was then also stopped. A maturing step was carried out for 15 minutes at pH 9, while progressively increasing the temperature (over 15 minutes) from 80 to 90° C., at which value the rest of the reaction was carried out.

Next, the pH was brought to pH 8 by introducing sulphuric acid having a concentration of 80 g/l. There was then a new simultaneous addition, carried out over 50 minutes, of sodium silicate at a rate of 50 g/min (the same sodium silicate as in the first simultaneous addition) and of sulphuric acid, with a concentration of 80 g/l, at a rate set so as to maintain the pH of the reaction mixture at a value of 8.

After this simultaneous addition, the reaction mixture is taken to a pH of 4 by sulphuric acid having a concentration of 80 g/l. The mixture is matured for 10 minutes at pH 4.

The slurry was filtered and washed under vacuum (16.8% cake solids content). After dilution (10% solids content), the cake obtained was mechanically broken up. The resulting slurry was spray dried by means of a turbine spray dryer.

The characteristics of the silica P6 obtained were then the following:

CTAB specific surface area: 170 m²/g;
BET specific surface area: 174 m²/g;
$V_{(d5-d50)}/V_{d5-d100)}$: 0.78;
Width $L_d$ (XDC): 3.1;
Pore distribution width ldp: 1.42;
Width $L'_d$ (XDC): 2.27;
Sears number×1000/BET specific surface area: 50.6;
XDC mode: 41 nm;
Pore volume $V_{80}$: 1.38 cm³/g;
$Ø_{50S}$ (after ultrasonic disintegration): 4.3 μm;
$F_{DS}$: 3.7 ml;
α: 0.00883 . μm⁻¹.μm⁻¹;
$d_w$: 98 nm;
W/FI: 0.78;
$N_{SiOH/nm}^2$: 4.40.

Example 8

Introduced into a 2000 litre reactor were 700 litres of industrial water. This solution was heated to 80° C. by direct injection heating of steam. Sulphuric acid, with a concentration of 80 g/l, was introduced, with stirring (95 rpm), until the pH reached a value of 4.

Simultaneously introduced into the reactor over 35 minutes were a sodium silicate solution (having an $SiO^2/Na^2O$ weight ratio of 3.52) having a concentration of 230 g/l at a rate of 190 l/hour and sulphuric acid, having a concentration of 80 g/l, at a rate set so as to maintain the pH of the reaction mixture at a value of 4.

After 35 minutes of simultaneous addition, the introduction of acid was stopped when the pH reached a value of 8. There was then a new simultaneous addition, carried out over 40 minutes, of sodium silicate at a rate of 190 l/hour (the same sodium silicate as in the first simultaneous addition) and of sulphuric acid, with a concentration of 80 g/l, at a rate set so as to maintain the pH of the reaction mixture at a value of 8.

After this simultaneous addition, the reaction mixture is taken to a pH of 5.2 by sulphuric acid having a concentration of 80 g/l. The mixture is matured for 5 minutes at pH 5.2.

The slurry was filtered and washed in a filter press (22% cake solids content). The cake obtained was broken up by adding a quantity of sodium aluminate corresponding to an Al/SiO₂ weight ratio of 0.3%. The resulting slurry was spray dried by means of a nozzle spray drier.

The characteristics of the silica obtained P7 in the form of approximately spherical beads were then the following:

CTAB specific surface area: 200 m²/g;
BET specific surface area: 222 m²/g;
$V_{(d5-d50)}/V_{(d5-d100)}$: 0.71;
Width $L_d$ (XDC): 1.0;

Pore distribution width ldp: 1.51;
Width $L'_d$ (XDC): 0.93;
Sears number×1000/BET specific surface area: 31.5;
XDC mode: 34 nm;
Pore volume $V_{80}$: 1.44 cm$^3$/g;
Mean particle size: >150 µm;
$Ø_{50S}$ (after ultrasonic disintegration): 4.8 µm;
$F_{DS}$: 5.4 ml;
$Ø_{50M}$ (after ultrasonic disintegration): 5.0 . µm;
$F_{Dm}$: 11.5;
α: 0.00566 µm$^{-1}$.min$^{-1}$;
$d_w$: 68 nm;
W/FI: 0.70;
$N_{SiOH/nm^2}$: 4.50.

Example 9

Introduced into a 2000 litre reactor were 700 litres of industrial water. This solution was heated to 78° C. by direct steam injection heating. Sulphuric acid, with a concentration of 80 g/l, was introduced, with stirring (95 rpm), until the pH reached a value of 4.

Simultaneously introduced into the reactor over 35 minutes were a sodium silicate solution (having an SiO$_2$/Na$_2$O weight ratio of 3.52) having a concentration of 230 g/l at a rate of 190 l/hour and sulphuric acid, having a concentration of 80 g/l, at a rate set so as to maintain the pH of the reaction mixture at a value of 4.

After 35 minutes of simultaneous addition, the introduction of acid was stopped when the pH reached a value of 8. There was then a new simultaneous addition, carried out over 40 minutes, of sodium silicate at a rate of 190 l/hour (the same sodium silicate as in the first simultaneous addition) and of sulphuric acid, with a concentration of 80 g/l, at a rate set so as to maintain the pH of the reaction mixture at a value of 8.

After this simultaneous addition, the reaction mixture is taken to a pH of 5.2 by sulphuric acid having a concentration of 80 g/l. The mixture is matured for 5 minutes at pH 5.2.

The slurry was filtered and washed in a vacuum filter (18% cake solids content). The cake obtained was broken up mechanically using industrial water (10% of water added with respect to the cake) by adding a quantity of sodium aluminate corresponding to an Al/SiO$^2$ weight ratio of 0.3%. The resulting slurry was spray dried by means of a turbine spray drier.

The characteristics of the silica obtained P8 were then the following:
CTAB specific surface area: 194 m$^2$/g;
BET specific surface area: 212 m$^2$/g;
$V_{(d5-d50)}/V_{(d5-100)}$: 0.75;
Width $L_d$ (XDC): 1.11;
Pore distribution width ldp: 0.83;
Width $L'_d$ (XDC): 4.29;
Sears number×1000/BET specific surface area: 34.9;
XDC mode: 47 nm;
Pore volume $V_{80}$: 1.37 cm$^3$/g;
$Ø_{50S}$ (after ultrasonic disintegration): 5.9 µM;
α.: 0.00396 µm$^{-1}$.min$^{-1}$.

Example 10

Two polymer compositions were prepared:
one containing highly dispersible precipitated silica Z1165MP, sold by Rhodia (the characteristics of which were mentioned in Example 6), and a coupling agent (reference composition R2);
the other containing silica prepared in Example 8 and a coupling agent (composition C3).

TABLE 3

(compositions in parts by weight)

|  | Composition R2 | Composition C3 |
|---|---|---|
| BR[1] | 70 | 70 |
| SBR[2] | 15 | 15 |
| NBR[3] | 15 | 15 |
| Silica Z1165MP | 50 | 0 |
| Silica of Example 8 | 0 | 50 |
| SILQUEST A1891[4] | 1 | 1 |
| Liquid paraffin[5] | 10 | 10 |
| Searic acid | 1.5 | 1.5 |
| Zinc oxide | 3 | 3 |
| Polyethylene glycol[6] | 3 | 3 |
| TBBS[7] | 1 | 1 |
| TBzTD[8] | 0.6 | 0.6 |
| Sulphur | 1.5 | 1.5 |

[1]Polybutadiene (KOSYN KBR01 type); .
[2]Solution-synthesized styrene-butadiene copolymer (BUNA VSL 5025 type) not oil-extended;
[3]Butadiene-acrylonitrile copolymer (KRYNAC 34-50 type); .
[4]γ-Mercaptopropyltriethoxysilane filler/polymer coupling agent (sold by Crompton);
[5]PLASTOL 352 (sold by Exxon); .
[6]PEG 4000 type (sold by Hüls); .
[7]N-tert-butylbenzothiazyl sulphenamide;
[8]Tetrabenzylthiuram disulphide.

The compositions were prepared by thermomechanically working the elastomers in an internal mixer (Banbury type) having a volume of 1200 cm$^3$. The initial temperature and the speed of the rotors were set so as to achieve drop temperatures of the compounds of about 120° C. This step was followed by a finishing step carried out on an external mixer at temperatures below 110° C. This phase allowed the vulcanization system to be introduced.

The vulcanization temperature was chosen to be 160° C. The vulcanization conditions for the compositions were tailored to the vulcanization rates of the corresponding mixtures.

The properties of the compositions are given below, the measurements having been carried out according to the following standards and/or methods:

Vulcanization Properties (Rheological Properties)
(Green Properties—Rheometry at 160° C., t=30 minutes)
NF T 43015 standard.

A Monsanto 100 S rheometer was used especially for the measurement of the minimum torque ($C_{min}$) and the maximum torque ($C_{max}$).

Ts2 corresponded to the time over which it was possible to monitor the mixture; the polymer mixture cured after Ts2 (start of vulcanization).

T90 corresponded to the time it took for the mixture to undergo 90% vulcanization.

Mechanical Properties (of the Compositions Vulcanized at 160° C.)

Tensile properties (moduli, tensile strength and elongation at break): NF T 46002 standard The x % moduli corresponded to the stress measured at a tensile strain of x %.

Tear strength: NF T 46007 (method B) standard.

Shore A hardness: ASTM D2240 standard; the value in question is measured 15 seconds after application of the force.

Abrasion resistance: DIN 53516 standard; the measured value is the abrasion loss: the lower the loss, the better the abrasion resistance.

TABLE 4

|  | Composition R2 | Composition C3 |
| --- | --- | --- |
| Vulcanization |  |  |
| Cmin (in · lb) | 22 | 28 |
| Ts2 (min) | 0.8 | 1.4 |
| T90 (min) | 3.3 | 2.8 |
| $C_{max}$ (in · lb) | 96 | 95 |
| Mechanical |  |  |
| 10% modulus (MPa) | 0.8 | 0.8 |
| 100% modulus (MPa) | 2.8 | 3.1 |
| 300% modulus (MPa) | 9.0 | 8.9 |
| Tensile strength (MPa) | 11.9 | 12.8 |
| Elongation at break (%) | 377 | 418 |
| Tear strength (No. 10 notch) (kN/m) | 68 | 73 |
| Shore A hardness (pts) | 68 | 70 |
| Abrasion loss (mm³) | 36 | 29 |

It may be seen that composition C3 containing a silica according to the invention exhibits a particularly beneficial compromise of properties compared with that of reference composition R2.

While still having a vulcanization rate comparable to that of reference composition R2 and moduli similar to those of reference composition R2, composition C3 possesses a tensile strength, an elongation at break, a tear strength and a Shore hardness that are superior to those of reference composition R2. Above all, composition C3 has an abrasion resistance very much higher than reference composition R2: the abrasion loss is thus reduced by almost 20%.

Example 13

Three polymer compositions were prepared:

one containing highly dispersible precipitated silica Z1165MP, sold by Rhodia (the characteristics of which were mentioned in Example 6), and a coupling agent (reference composition R3);

the other two containing silica prepared in Example 8 and a coupling agent (composition C4), or silica prepared in Example 9 and a coupling agent (composition C5).

TABLE 5

(compositions in parts by weight)

|  | Composition R3 | Composition C4 | Composition C5 |
| --- | --- | --- | --- |
| SBR[1] | 103 | 103 | 103 |
| BR[2] | 25 | 25 | 25 |
| Silica Z1165MP | 80 | 0 | 0 |
| Silica of Example 8 | 0 | 80 | 0 |
| Silica of Example 9 | 0 | 0 | 80 |
| TESPT[3] | 6.4 | 8.0 | 7.7 |
| Stearic acid | 2.0 | 2.0 | 2.0 |
| Zinc oxide | 2.5 | 2.5 | 2.5 |
| Antioxidant[4] | 1.9 | 1.9 | 1.9 |
| DPG[5] | 1.5 | .18 | 1.8 |
| CBS[6] | 2.0 | 2.0 | 2.0 |
| Sulphur | 1.1 | 1.1 | 1.1 |

[1]Solution-synthesized styrene-butadiene copolymer (BUNA VSL 5025-1 type), oil-extended (37.5% by weight);
[2]Polybutadiene (BUNA CB24 type sold by Bayer);
[3]Filler/polymer coupling agent: bis(3-(triethoxysilyl)prop-yl tetrasulphide (sold by Degussa under the name Si69); .
[4]N-1,3-dimethylbutyl-N-phenyl-para-phenylenediamine (SANTOFLEX 6-PPD sold by Flexsys); .
[5]Diphenylguanidine (VULKACIT D sold by Bayer);
[6]N-cyclohexyl-2-benzothiazyl sulphenamide (SANTOCURE sold by Flexsys).

Each of the three compositions was prepared in three successive phases. The first two phases, carried out in an internal mixer, allowed thermomechanical working at high temperature until a maximum temperature of about 150° C. was obtained. They were followed by a third mechanical working phase carried out on cylinders at temperatures below 110° C. The latter phase allowed the vulcanization system to be introduced.

The mixer employed for the first two phases was an internal mixer of the Brabender type, with a capacity of 70 cm³. The initial temperature and the speed of the rotors were set each time so as to achieve drop temperatures of the compound close to 150° C. The first step made it possible to incorporate the elastomers (at $t_0$), the silica (divided introduction, ⅔ then ⅓) with the coupling agent (at $t_0$+2 min), then with the DPG (at $t_0$+4 min) and finally the stearic acid (at $t_0$+6 min). After discharge from the mixer (compound drop at $t_0$+7 min), followed by compound cooling (temperature below 100° C.) and reintroduction (at $t'_0$) into the internal mixer (the temperature then progressively rising), a second step in this mixer made it possible, by a thermomechanical treatment, to improve the dispersion of the silica and of its coupling agent in the elastomeric matrix. During this step, the zinc oxide and the antioxidant were incorporated (at $t'_0$+1 min).

After discharge from the mixer (compound drop at $t'_0$+4 min) followed by cooling of the compound (temperature below 100° C.), the third phase made it possible to introduce the vulcanization system (sulphur and CBS). It was carried out on a cylinder mixer preheated to 50° C. The duration of this phase was between 5 and 20 minutes.

After homogenization and finish passes, each final compound was calendered in the form of sheets 2-3 mm in thickness.

The vulcanization temperature was chosen to be 160° C. The vulcanization conditions for the compositions were tailored to the vulcanization rates of the corresponding compounds.

The properties of the compositions are given below, the measurements having been carried out according to the standards and/or methods indicated in Example 10. The dynamic properties (of the compositions vulcanized at 160° C.), such as the tan δ at 60° C., were determined on a METRAVIB VA3000 viscoelasticimeter, according to the ASTM D5992 standard, with a 4% prestrain and a frequency of 10 Hz (sinusoidal wave).

TABLE 6

|  | Composition R3 | Composition C4 | Composition C5 |
| --- | --- | --- | --- |
| Vulcanization |  |  |  |
| Cmin (dN · m) | 25 | 33 | 27 |
| Ts2 (min) | 3.9 | 3.8 | 4.1 |
| T90 (min) | 14.2 | 16.3 | 15.2 |
| $C_{max}$ (dN · m) | 71 | 76 | 75 |
| Mechanical |  |  |  |
| 10% modulus (Mpa) | 0.6 | 0.7 | 0.6 |
| 100% modulus (Mpa) | 2.4 | 2.8 | 2.9 |
| 200% modulus (Mpa) | 6.4 | 7.4 | 7.2 |
| Shore A hardness (pts) | 62 | 67 | 67 |
| Abrasion loss (mm³) | 72 | 56 | 58 |
| Dynamic |  |  |  |
| tanδ (60° C.) | 0.121 | 0.113 | 0.100 |

It may be seen that compositions C4 and C5 each containing a silica according to the invention exhibit a particularly beneficial compromise of properties compared with that of reference composition R3.

While still having a vulcanization rate comparable to that of reference composition R3, compositions C4 and C5 possess moduli and a Shore hardness higher than those of reference composition R3. Above all, compositions C4 and C5 exhibit a much higher abrasion resistance than reference composition R3: the abrasion loss is thus reduced by about 20%. Finally, compositions C4 and C5 possess a lower tan δ at 60° C. than reference composition R3, it also proving to be particularly beneficial in the case of the properties of finished articles based on these compositions C4 or C5.

What is claimed is:

1. A silica, having:
    a CTAB specific surface area ($S_{CTAB}$) of 95 to 525 m$^2$/g;
    a BET specific surface area ($S_{BET}$) of 45 to 550 m$^2$/g;
    a size distribution width $L_d$ ((d84−d16)/d50) of objects measured by XDC particle size analysis after ultrasonic disintegration in water of at least 0.91;
    a pore volume distribution having a ratio $V_{(d5-d100)}/V_{(d5-d100)}$ of at least 0.66; and
    a pore distribution width Ldp of greater than 0.70.

2. The silica according to claim 1, wherein the size distribution width $L_d$ ((d84−d16)/d50) of objects is of at least 0.94, and wherein the pore volume distribution having the ratio $V_{(d5-d50)}/V_{(d5-d100)}$ is at least 0.68.

3. The silica according to claim 2, wherein the pore volume distribution having the ratio $V_{(d5-d50)}/V_{(d5-d100)}$ is at least 0.73.

4. The silica according to claim 1, wherein the size distribution width Ld ((d84−d16)/d50) of objects measured by XDC particle size analysis after ultrasonic disintegration in water, is of at least 1.04, and the pore volume distribution such that the ratio $V_{(d5-d50)}/V_{(d5-d100)}$ is at least 0.71.

5. The silica according to claim 1, wherein, after ultrasonic disintegration in water, the silica has a median diameter ($ø_{50S}$) and a median diameter ($ø_{50M}$) of less than 8.5 µm.

6. The silica according to claim 5, wherein, after ultrasonic disintegration in water, the median diameter ($ø_{50S}$) is less than 6.0 µm.

7. The silica according to claim 1, wherein the silica has a rate of disintegration, denoted by α, measured in the test referred to as ultrasonic disintegration in water in pulsed mode, at 100% power of a 600 watt probe, of at least 0.0035 µm$^{-1}$.min$^{-1}$.

8. The silica according to claim 1, further comprising a size distribution width $L'_d$ ((d84−d16)/d50) of objects measured by XDC particle size analysis after ultrasonic disintegration in water smaller than 500 nm of at least 0.95.

9. The silica according to claim 1, wherein the silica has a (Sears number×1000)/(BET specific surface area ($S_{BET}$)) ratio of less than 60.

10. The silica according to claim 1, wherein the silica has a pore volume ($V_{80}$) formed by the pores having a diameter of 3.7 to 80 nm of at least 1.35 cm$^3$/g.

11. The silica according to claim 1, wherein the CTAB specific surface area ($S_{CTAB}$) is 95 to 330 m$^2$/g; and the BET specific surface area ($S_{BET}$) of between 70 and 350 m$^2$/g.

12. The silica according to claim 1, wherein the CTAB specific surface area ($S_{CTAB}$) is 95 to 230 m$^2$/g.

13. The silica according to claim 1, wherein the BET specific surface area ($S_{BET}$) is 110 to 270 m$^2$/g.

14. The silica according to claim 1, wherein the silica has a ($S_{BET}$)−($S_{CTAB}$)>5 m$^2$/g 45 and 550 m$^2$g.

15. The silica according to claim 1, wherein the silica has a form having at least one of: (a) approximately spherical beads having a mean size of at least 80 µm; (b) a powder having a mean size of at least 15 µm; and (c) granules having a mean size of at least 1 mm.

16. A polymer composition comprising a filler, the filler comprising the silica of claim 1.

17. An article of manufacture comprising the polymer composition of claim 16, the article comprising a shoe sole, a floor covering, a gas barrier, a fire-retardant material, a cable car wheel, a seal for electrical appliances, a seal for liquid or gas pipes, a seal for a brake system, a sheath, a duct, a cable or a drive belt.

18. An article of manufacture comprising the silica of claim 1, the article comprising a catalyst support, and absorbent for active materials, a viscosity-modifying material, a texturing or anti-clumping agent, an element for a battery separator, an additive for dentrifice, or an additive for paper.

19. A process for preparing the silica of claim 1, comprising a reaction of a silicate with an acidifying agent whereby a silica suspension is obtained, followed by a separation and a drying of the silica suspension, said reaction of the silicate with the acidifying agent being carried out according to the following successive steps:
    (i) forming an aqueous stock having a pH of between 2 and 5;
    (ii) adding simultaneously the silicate and the acidifying agent to the aqueous stock forming a reaction mixture in such a way that the pH of the reaction mixture is maintained between 2 and 5;
    (iii) stopping addition of the acidifying agent, while continuing to add the silicate into the reaction mixture until the pH of the reaction mixture of between 7 and 10 is obtained;
    (iv) adding simultaneously the silicate and the acidifying agent to the reaction mixture in such a way that the pH of the reaction mixture is maintained between 7 and 10; and
    (v) stopping addition of the silicate, while continuing to add the acidifying agent into the reaction mixture until the pH of the reaction mixture of less than 6 is obtained.

20. The process according to claim 19, wherein a maturing step is carried out between step (iii) and step (iv).

21. The process according to claim 19, wherein a maturing step is carried out after step (v).

22. The process according to claim 19, wherein, in step (v), the addition of the silicate is stopped, while continuing to add the acidifying agent into the reaction mixture until a pH value of the reaction mixture of between 3 and 5.5 is obtained.

23. The process according to claim 19, wherein, between step (iii) and step (iv), the acidifying agent is added to the reaction mixture, and the pH of the reaction mixture after addition of the acidifying agent is between 7 and 9.5.

24. The process according to claim 19, wherein the reaction between the silicate and the acidifying agent in steps (i) to (v) is carried out between 70 and 95° C.

25. The process according to claim 19, wherein the reaction between the silicate and the acidifying agent in steps (i) to (v) is carried out at a constant temperature.

26. The process according to claim 19, wherein forming the aqueous stock in step (i) comprises addition of the acidifying agent to water to obtain a pH value of the aqueous stock between 2 and 5.

27. The process according to claim 19, wherein forming the aqueous stock in step (i) comprises addition of the acidifying agent to a mixture of water and silicate to obtain a pH value of the aqueous stock between 2 and 5.

28. The process according to claim 19, wherein the drying is carried out by spray drying.

29. The process according to claim 19, wherein the separation comprises a filtration carried out by a filter press.

30. The process according to claim 19, wherein the drying is carried out by a nozzle spray dryer.

31. The process according to claim 19, wherein the separation comprises a filtration carried out by a vacuum filter.

32. The process according to claim 19, wherein the drying is carried out by a turbine spray dryer.

33. A silica, having:
- a CTAB specific surface area ($S_{CTAB}$) of 95 to 525 m$^2$/g;
- a BET specific surface area ($S_{BET}$) of 45 to 550 m$^2$/g;
- a size distribution width $L'_d$ ((d84−d16)/d50) of objects smaller than 500 nm, measured by XDC particle size analysis after ultrasonic disintegration in water, of at least 0.90; and
- a pore volume distribution having a ratio $V_{(d5-d50)}/V_{(d5-d100)}$ of at least 0.71.

34. The silica according to claim 33, wherein, after ultrasonic disintegration in water, the silica has a median diameter ($ø_{50S}$) of less than 8.5 µm.

35. The silica according to claim 33, wherein the silica has a rate of disintegration, denoted by a, measured in the test referred to as ultrasonic disintegration in water in pulsed mode, at 100% power of a 600 watt probe, of at least 0.0035 µm$^{-1}$·min$^{-1}$.

* * * * *

UNITED STATES PATENT AND TRADEMARK OFFICE
CERTIFICATE OF CORRECTION

PATENT NO. : 11,241,370 B2
APPLICATION NO. : 13/166458
DATED : February 8, 2022
INVENTOR(S) : Remi Valero et al.

Page 1 of 1

It is certified that error appears in the above-identified patent and that said Letters Patent is hereby corrected as shown below:

In the Claims

At Column 27, Claim number 1, Line numbers 20-21, the ratio "$V_{(d5-d100)}/V_{(d5-d100)}$" should read -- $V_{(d5-d50)}/V_{(d5-d100)}$ --.

At Column 27, Claim number 14, Line number 64, "45 and 550 m²g" should read -- and < 50 m²/g --.

At Column 29, Claim number 34, Line number 23, "$\varnothing_{50S}$" should read -- $\varnothing_{50M}$ --.

Signed and Sealed this
Twenty-fourth Day of May, 2022

Katherine Kelly Vidal
*Director of the United States Patent and Trademark Office*